United States Patent [19]

Zoltan

[11] Patent Number: 4,535,782

[45] Date of Patent: Aug. 20, 1985

[54] METHOD FOR DETERMINING WOUND VOLUME

[75] Inventor: Bart J. Zoltan, Old Tappan, N.J.

[73] Assignee: American Cyanamid Company, Stamford, Conn.

[21] Appl. No.: 586,895

[22] Filed: Mar. 7, 1984

[51] Int. Cl.³ .............................................. A61B 5/00
[52] U.S. Cl. ................................................... 128/665
[58] Field of Search ................ 128/665, 630; 356/433, 356/435, 436, 376

[56] References Cited

U.S. PATENT DOCUMENTS

| | | | |
|---|---|---|---|
| 3,612,693 | 10/1971 | Stenson | 356/376 |
| 3,627,427 | 12/1971 | Johnson | 356/376 |
| 3,814,521 | 6/1974 | Free | 356/376 |
| 4,050,821 | 9/1977 | Cuthbert et al. | 356/433 |
| 4,234,253 | 11/1980 | Higginbotham et al. | 356/435 |
| 4,448,534 | 5/1984 | Wertz et al. | 356/436 |

*Primary Examiner*—Kyle L. Howell
*Assistant Examiner*—Ruth S. Smith
*Attorney, Agent, or Firm*—Charles F. Costello, Jr.

[57] ABSTRACT

A non-contacting volume determination method for use on wounds, having a known pattern of lines optically projected onto the volume to be determined. The image of the projection viewed from an angle other than the projection axis, along with the image of a reference volume located near the volume to be determined, are used to accurately determine the unknown volume.

10 Claims, 4 Drawing Figures

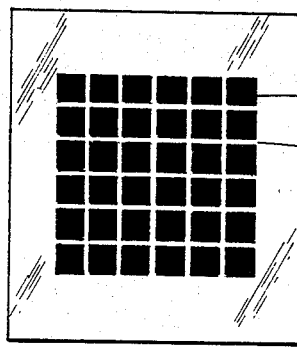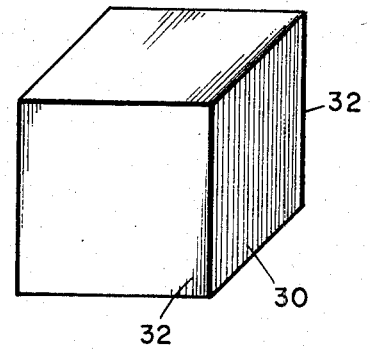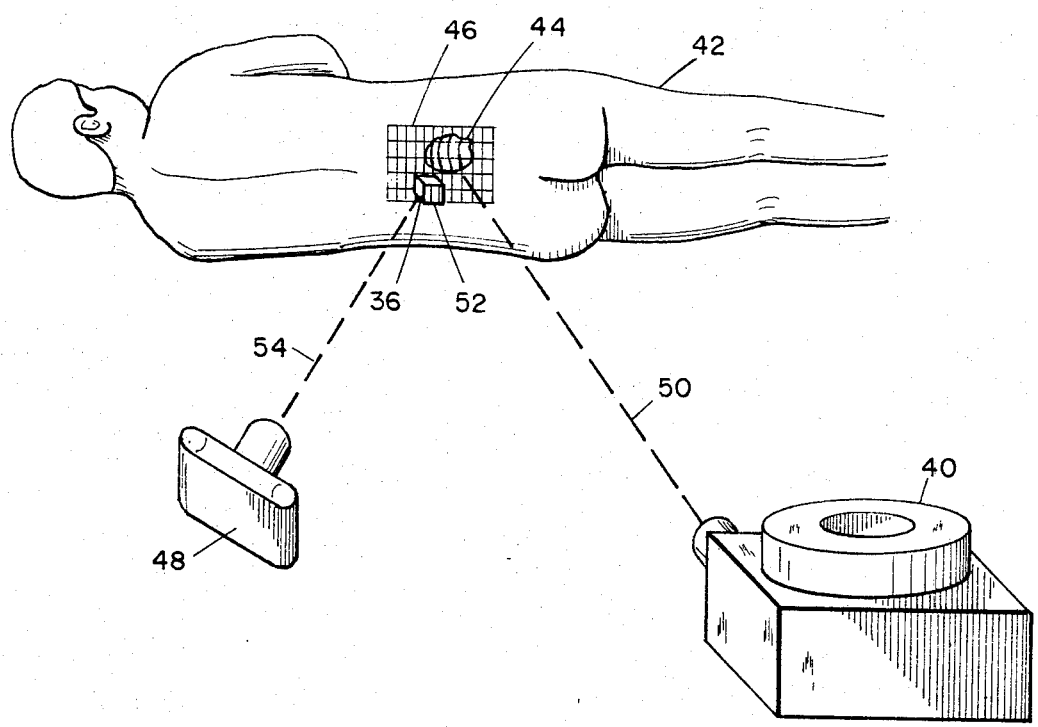

METHOD FOR DETERMINING WOUND VOLUME

FIELD OF THE INVENTION

This invention relates to the determination of volumes, specifically, to the non-contacting measurement of wound volumes.

BACKGROUND OF THE INVENTION

In the medical treatment of patients with decubitus ulcers, also referred to as bedsores or pressure sores, it is known that an indication of treatment efficacy is the reduction of the volume of the wound. The wound is usually recessed, where healthy tissue has died, and necrotic tissue or flesh is visible. It has been recognized that a rapid indication of wound volume has a place in the confirmation of the efficacy of the treatment for decubitus ulcers and the like.

Previous methods of measuring wound volume required the use of expensive stereophotogrammetric instrumentation, which also required precision in the set-up of the equipment. The previous methods entailed the use of two cameras positioned at precisely know angles relative to the wound, and relative to each other. The negatives of images taken through the two cameras would then be mounted on a stereophotogrammetric viewer which was manually manipulated to yield measurements. "Evaluation of Leg Ulcer Treatment with Stereophotogrammetry", G. Eriksson et al, British Journal of Dermatology 101, 123 (1979) gives details of this method. Another prior method, "Acceleration of Wound Healing in Man with Zinc Sulfate Given by Mouth", W.J. Pories et al, The Lancet 1, 7482, (1967), involved the making of a cast of the wound and then weighing the cast. The cast method is very painful and uncomfortable to the patient, and cannot be used repeatedly on the same patient. Another method includes the use of water or other liquid poured onto the wound. The volume of the liquid used is then measured to determine the volume of the wound. The average physician, even the dermatological specialist lacked the expertise and the time to use these prior art methods.

There are certain desirable characteristics of methods to measure wound volume. The method should be as painless to the patient as possible. The method should require minimum repositioning of the patient. Contact with the wound should be avoided. The accuracy of the method should be sufficient to indicate improvement of the wound status as soon as possible. The time between the collection of data, and the availability of results should be minimal.

It is with this background that the invention was developed during a program to validate the efficacy of a treatment for decubitus ulcers.

SUMMARY OF THE INVENTION

The wound to be measured is located, and a projector is set up with its optical axis perpendicular to the wound. The projector is focused to project onto the wound to be measured a grid of bright lines. A reference cube is placed next to the wound and in the plane of the wound. This reference cube has dimensions which are known. The wound and the reference cube are photographed from a location off the projector axis, and with the camera axis parellel to two sides of the reference cube.

The photograph thus taken has lines manually drawn upon it to complete the path the projected lines would have taken were the wound not present. The area enclosed by the actual path of the projected line and the path were the wound not present is measured. The sum of these areas is then found. The area of the reference cube face parallel to the above areas is similarly measured. Since the area of the reference face is known, the other measured areas are referred back to the reference cube. Using the length of the edge of the reference cube parallel to the camera optical axis, the distance between the lines of the grid going away from the camera is determined. In this way, the areas of "slices" and the distance between these "slices" are found. The volume is the product of the areas and the distance between the projected grid lines perpendicular to the camera axis.

In a preferred embodiment, the grid is a square array of lines, and the reference cube has faces which have exactly a 10 cm$^2$ area.

The means of area measurement in the preferred embodiment is a digitizing pad used in conjunction with a small computer.

A method of determining the volume of a wound has been invented. The method comprises:
(a) placing a reference volume of known geometry adjacent a wound,
(b) projecting a pattern of lines onto the wound,
(c) imaging the wound from the projecting step with means for imaging,
(d) obtaining the image from the imaging step,
(e) measuring the area of said image bounded by the projected pattern of the lines on the wound surface, and by the projected pattern of the lines were said wound not present, and
(f) using the areas from the measuring step and the reference volume to calculate the volume of the wound.

In one embodiment, the reference volume is a cube. In another embodiment, the reference volume is a rectangular prism. In yet another embodiment, the pattern of lines is a grid. In a further embodiment, the imaging means is a photographic camera, or a television camera.

A method of determining the volume of a decubitus ulcer wound has also been invented. The method comprises:
(a) placing a cube of known geometry next to a wound, with at least one surface of the cube being co-planar with the wound,
(b) projecting the parallel image of a square grid of lines onto the wound with means for projecting,
(c) photographing the wound, the reference cube, and the square grid of projected lines from an oblique angle to the axis of projection,
(d) either simultaneously, sequentially or reverse sequentially:
   (I) measuring the area of said image bounded by the locus of the projected pattern of lines upon said wound surface, and by the locus of the lines were the wound not present,
   (II) measuring the area of said image of the side of the reference cube that is co-planar with the wound, and
(e) using the area from the measuring sub-step II to normalize the areas from the measuring sub-step I and
(f) determining said volume by multiplying the sum of the areas obtained in step (e) by the distance between the projected lines.

BRIEF DESCRIPTION OF THE DRAWINGS

FIG. 1 is the transparency used to project a grid of lines.

FIG. 2 is the reference cube used as a scale within the photograph.

FIG. 3 shows the set-up with the patient, the projector and the camera.

DETAILED DESCRIPTION OF THE PREFERRED EMBODIMENT

Figure 4:
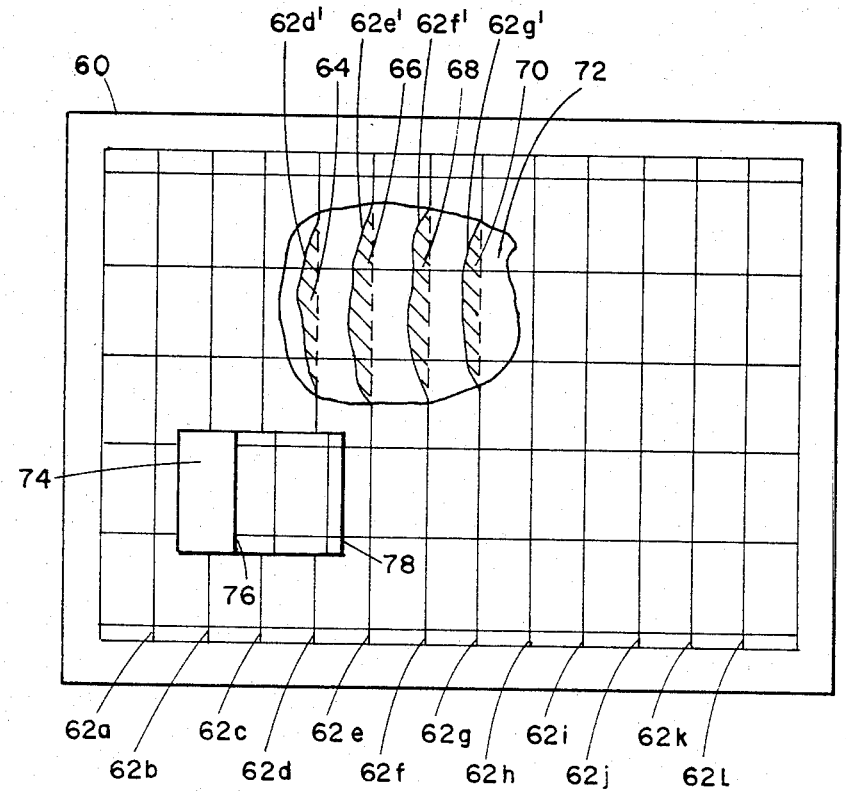
FIG. 4 shows a typical photograph taken with the set-up of FIG. 3.

In the preferred embodiment, as shown in FIG. 1, a photographic transparency, suitable for projection 20 is made having an essentially dark background 22 and a square grid of clear lines 24.

In order to insert scale into the system, a reference cube 30 is made with faces and edges of exactly known dimensions. See FIG. 2. In the preferred embodiment each face of the cube is exactly 10 cm². The cube is white, and in order to enhance the outline of the cube, each edge 32 is outlined in black.

In use, FIG. 3, the patient is located with the wound 44 perpendicular to the optical axis 50 of the projector 40. The projector is used to project the pattern of perpendicular grid lines of the transparency 20. The reference cube 30 is located near the wound, with one face 52, perpendicular to projector axis 50, and with the edges of that face 52 parallel to the projected grid lines 46.

The camera 48 is located off the projector axis 50, and is pointed at the wound volume to be determined. The camera axis 54 is located so that the plane made by it and the projector axis 50 is parallel to two of the planes of the reference cube 30.

With the set-up as described, the camera 48 is used to photograph the wound 44, with the grid lines 46 projected onto the wound, and with the reference cube 30 included in the photograph.

FIG. 4 is a representation of such a photograph. The photograph 60, contains an image of the wound 72, and an image of the reference cube 30. Because the photograph is taken at an angle off the projector axis 50 the image of the cube, and of the wound are both distorted in exactly the same manner. One face 74 of the cube is perpendicular to the wound, and is visible in the photograph 60. In the photograph of the projected grid lines 62a, 62b, 62c, 62d, 62e, 62f, 62g, 62h, 62i, 62j, 62k, and 62l, lines 62d, 62e, 62f, and 62g are distorted because they fall into the depression of the wound volume to be determined.

It is necessary to mark the location of where these distorted lines would have fallen were the wound not present. These broken lines are shown as 62d, 62e, 62f, and 62g. Each of the areas between the respective projected line and its "primed" locus (i.e. 62d 62d') is measured. As shown in FIG. 4, the area between 62d and 62d' is labeled 64, between 62e and 62e' is 66, between 62f is 68, and between 62g and 62g' is 70.

The measured areas 64, 66 68, and 70, can be normalized to actual areas in the field of view instead of areas in a photograph by using the area 74 of the reference cube as a standard. In this way the wound was effectively "sliced" into equi-spaced slices, and the area of each slice was measured.

In order to determine the volume of the wound it is necessary to also determine the thickness of the slices. Once again, the image of the reference cube 30 in the photograph 60 is used to determine scale. The distance between the edges 76, and 78 of the cube, of the face which lies parallel to the plane of the wound, and which is visible in the photograph is exactly the square root of the area of the reference face, in our case 3.16 cm.

This measurement can be used to determine exactly the distance between any adjacent projected lines, for example 62e to 62f. With the knowledge of the distance between projected lines, the thickness of the "slices" of the wound is readily determined. In order to determine the wound volume it is only necessary to multiply the sum of the areas by the distance between the projected lines.

As shown in FIGS. 3 and 4, the grid is a pattern of black lines on a white background surface. It is to be understood that these figures are for illustration of the invention only. That is, in the actual preferred embodiment and to be consistent with FIG. 1, the actural pattern of lines will be white (i.e., clear) and the background surface will be black (i.e., dark).

I claim:

1. A method of determining the volume of a wound comprising:
    (a) placing a reference volume of known geometry adjacent a wound,
    (b) projecting a pattern of lines onto said wound and unto an area contiguous with said wound,
    (c) imaging said wound and said contiguous area from said projecting step, with means for imaging,
    (d) obtaining the image from said imaging step,
    (e) measuring the area of said image bounded by the projected pattern of the lines on said wound surface, and by the projected pattern of the lines were said wound not present, and
    (f) using the areas from said measuring step and said reference volume to calculate said volume of said wound.

2. The method of claim 1 step (a) comprising placing a cube adjacent a wound.

3. The method of claim 1 step (a) comprising placing a rectangular prism adjacent a wound.

4. The method of claim 2 step (b) comprising projecting a grid onto said wound.

5. The method of claim 3 step (c) comprising imaging said wound and said contiguous area from said projecting step, with a photographic camera.

6. The method according to claim 3 step (c) comprising imaging said wound and said contiguous area from said projecting step, with a television camera.

7. A method of determining a volume of a decubitus ulcer wound, comprising:
    (a) placing a cube of known geometry next to a wound, with at least one surface of said cube being co-planar with said wound,
    (b) projecting a parallel image of a square grid of lines onto said wound with means for projecting,
    (c) photographing said wound, said reference cube, and said square grid of projected lines from an oblique angle to the axis of projection,
    (d) measuring the area of said image bounded by the locus of said projected pattern of lines upon said wound surface, and by the locus of said lines were said wound not present,
    (II) measuring the area of said image of the side of said reference cube that is co-planar with said wound, and (e) using said area from said measuring sub-step II to normalize the areas from said measuring sub-step I and (f) determining said volume by multiplying the sum of the areas obtained in step (e) by the distance between the projected lines.

8. The method of claim 7 step (d) wherein said measuring sub-steps I and II are conducted simultaneously.

9. The method of claim 7 step (d) wherein said measuring sub-steps I and II are conducted sequentially.

10. The method of claim 7 step (d) wherein said measuring sub-steps I and II are conducted reverse sequentially.

* * * * *

UNITED STATES PATENT AND TRADEMARK OFFICE
CERTIFICATE OF CORRECTION

PATENT NO. : 4,535,782

DATED : August 20, 1985

INVENTOR(S) : Bart Joseph Zoltan

It is certified that error appears in the above-identified patent and that said Letters Patent is hereby corrected as shown below:

Claim 7, after (d) insert -- (I) --.

Signed and Sealed this

Twelfth Day of November 1985

[SEAL]

Attest:

Attesting Officer

DONALD J. QUIGG

Commissioner of Patents and Trademarks